US010188456B2

United States Patent
Prisco et al.

(10) Patent No.: US 10,188,456 B2
(45) Date of Patent: Jan. 29, 2019

(54) ELECTRODE ASSEMBLY FOR RF ENERGY ENABLED TISSUE DEBRIDEMENT DEVICE

(71) Applicant: Medtronic Xomed, Inc., Jacksonville, FL (US)

(72) Inventors: John R. Prisco, Jacksonville, FL (US); Eric P. Detmers, Jacksonville, FL (US); Wenjeng Li, Saint Johns, FL (US); David J. Little, Ponte Vedra Beach, FL (US); Patrick Richart, Jacksonville, FL (US); Jose Valdez, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 253 days.

(21) Appl. No.: 15/046,869

(22) Filed: Feb. 18, 2016

(65) Prior Publication Data
US 2016/0235474 A1 Aug. 18, 2016

Related U.S. Application Data

(60) Provisional application No. 62/117,541, filed on Feb. 18, 2015.

(51) Int. Cl.
A61B 18/14 (2006.01)
A61B 17/32 (2006.01)
A61B 18/00 (2006.01)

(52) U.S. Cl.
CPC .... *A61B 18/1485* (2013.01); *A61B 17/32002* (2013.01); *A61B 18/148* (2013.01);
(Continued)

(58) Field of Classification Search
CPC . A61B 18/14–18/1485; A61B 17/3202; A61B 2218/002; A61B 2018/00029;
(Continued)

(56) References Cited

U.S. PATENT DOCUMENTS 2,888,928 A 6/1959 Seiger
3,223,088 A 12/1965 Barber et al.
(Continued)

FOREIGN PATENT DOCUMENTS

EP 1201196 5/2002
EP 2044893 4/2009
(Continued)

OTHER PUBLICATIONS

Non-Final Office Action for U.S. Appl. No. 15/047,242 dated Jul. 10, 2018 (32 pages).
(Continued)

*Primary Examiner* — Daniel Fowler
*Assistant Examiner* — Katherine Maziarski
(74) *Attorney, Agent, or Firm* — Dicke, Billig & Czaja, PLLC

(57) ABSTRACT

A bipolar electrosurgical device is disclosed that operates in a mechanical cutting mode and a hemostasis mode. The device includes a housing and a blade assembly extending from the housing. The blade assembly forms a cutting tip and cutting window at a distal end region to provide mechanical cutting of tissue and first and second electrode assemblies to provide electrical energy to tissue. The first electrode assembly includes an outer shaft defining a first electrode surface and the second electrode assembly includes an electrode body extending along and electrically isolated from an outer shaft and defining a U-shape in cross section.

15 Claims, 9 Drawing Sheets

(52) U.S. Cl.
CPC ............ *A61B 2018/00208* (2013.01); *A61B 2018/00607* (2013.01); *A61B 2217/007* (2013.01); *A61B 2218/002* (2013.01)

(58) Field of Classification Search
CPC ............ A61B 2018/00589–2018/595; A61B 2018/00178; A61B 10/0233–10/04; H01R 23/26; H01R 24/38; H01R 39/08; H01R 39/12; H01R 39/34; H01L 24/67
See application file for complete search history.

(56) References Cited

U.S. PATENT DOCUMENTS

| | | | |
|---|---|---|---|
| 3,682,130 A | 8/1972 | Jeffers | |
| 3,750,650 A | 8/1973 | Ruttgers | |
| 3,886,944 A | 6/1975 | Jamshidi | |
| 3,955,284 A | 5/1976 | Balson | |
| 3,955,578 A | 5/1976 | Chamness | |
| 4,014,342 A | 3/1977 | Staub | |
| 4,060,088 A | 11/1977 | Morrison | |
| 4,174,713 A | 11/1979 | Mehl | |
| 4,195,637 A | 4/1980 | Gruntzig | |
| 4,207,897 A | 6/1980 | Lloyd | |
| 4,248,224 A | 2/1981 | Jones | |
| 4,651,734 A | 3/1987 | Doss | |
| 4,823,791 A | 4/1989 | D'Amelio et al. | |
| 4,878,493 A | 11/1989 | Pasternak | |
| 4,931,047 A | 6/1990 | Broadwin et al. | |
| 4,932,952 A | 6/1990 | Wojciechowicz | |
| 4,943,290 A | 7/1990 | Rexroth | |
| 4,950,232 A | 8/1990 | Ruzicka | |
| 4,985,030 A | 1/1991 | Melzer | |
| 4,998,933 A | 3/1991 | Eggers | |
| 5,112,299 A | 5/1992 | Pascaloff | |
| 5,190,541 A | 3/1993 | Abele | |
| 5,195,959 A | 3/1993 | Smith | |
| 5,230,704 A | 7/1993 | Moberg | |
| 5,234,428 A | 8/1993 | Kaufman | |
| 5,254,117 A | 10/1993 | Rigby | |
| 5,275,609 A | 1/1994 | Pingleton | |
| 5,281,215 A | 1/1994 | Milder | |
| 5,282,799 A | 2/1994 | Rydell | |
| 5,330,521 A | 7/1994 | Cohen | |
| 5,334,181 A | 8/1994 | Rubinsky | |
| 5,336,220 A | 8/1994 | Ryan | |
| 5,336,443 A | 8/1994 | Odashima | |
| 5,352,222 A | 10/1994 | Rydell | |
| 5,364,395 A * | 11/1994 | West, Jr. ......... | A61B 17/32002 604/22 |
| 5,376,078 A | 12/1994 | Dinger | |
| 5,383,874 A | 1/1995 | Jackson | |
| 5,385,148 A | 1/1995 | Lesh | |
| 5,395,312 A | 3/1995 | Desai | |
| 5,401,272 A | 3/1995 | Perkins | |
| 5,405,348 A | 4/1995 | Anspach | |
| 5,405,376 A | 4/1995 | Mulier | |
| 5,413,556 A | 5/1995 | Whittingham | |
| 5,417,709 A | 5/1995 | Slater | |
| 5,431,168 A | 7/1995 | Webster | |
| 5,431,649 A | 7/1995 | Mulier | |
| 5,441,503 A | 8/1995 | Considine | |
| 5,443,463 A | 8/1995 | Stern | |
| 5,445,638 A | 8/1995 | Rydell | |
| 5,460,629 A | 10/1995 | Shlain | |
| 5,490,819 A | 2/1996 | Nicholas | |
| 5,492,527 A | 2/1996 | Glowa | |
| 5,496,271 A | 3/1996 | Burton | |
| 5,505,700 A | 4/1996 | Leone | |
| 5,540,562 A | 7/1996 | Giter | |
| 5,540,708 A | 7/1996 | Lim | |
| 5,542,196 A | 8/1996 | Kantro | |
| 5,542,945 A | 8/1996 | Fritzsch | |
| 5,556,397 A | 9/1996 | Long | |
| 5,560,373 A | 10/1996 | De Santis | |
| 5,562,702 A | 10/1996 | Huitema | |
| 5,569,243 A | 10/1996 | Kortenbach | |
| 5,569,254 A | 10/1996 | Carlson | |
| 5,573,424 A | 11/1996 | Poppe | |
| 5,595,183 A | 1/1997 | Swanson | |
| 5,599,346 A | 2/1997 | Edwards | |
| 5,605,539 A | 2/1997 | Buelna | |
| 5,609,573 A | 3/1997 | Sandock | |
| 5,620,415 A | 4/1997 | Lucey | |
| 5,620,447 A | 4/1997 | Smith | |
| 5,647,869 A | 7/1997 | Goble | |
| 5,685,838 A | 11/1997 | Peters | |
| 5,688,267 A | 11/1997 | Panescu | |
| 5,697,536 A | 12/1997 | Eggers | |
| 5,712,543 A | 1/1998 | Sjostrom | |
| 5,713,942 A | 2/1998 | Stern | |
| 5,733,280 A | 3/1998 | Avitall | |
| 5,743,903 A | 4/1998 | Stern | |
| 5,766,167 A | 6/1998 | Eggers | |
| 5,792,167 A | 8/1998 | Kablik | |
| 5,797,905 A | 8/1998 | Fleischman | |
| 5,797,960 A | 8/1998 | Stevens | |
| 5,810,764 A | 9/1998 | Eggers | |
| 5,810,802 A | 9/1998 | Panescu | |
| 5,810,809 A | 9/1998 | Rydell | |
| 5,814,044 A | 9/1998 | Hooven | |
| 5,827,216 A | 10/1998 | Igo | |
| 5,836,947 A | 11/1998 | Fleischman | |
| 5,840,030 A | 11/1998 | Ferek Petric | |
| 5,843,021 A | 12/1998 | Edwards | |
| 5,843,152 A | 12/1998 | Tu | |
| 5,849,023 A | 12/1998 | Mericle | |
| 5,873,855 A | 2/1999 | Eggers | |
| 5,873,886 A | 2/1999 | Larsen | |
| 5,891,142 A | 4/1999 | Eggers | |
| 5,895,355 A | 4/1999 | Schaer | |
| 5,897,553 A | 4/1999 | Mulier | |
| 5,899,915 A | 5/1999 | Saadat | |
| 5,902,272 A * | 5/1999 | Eggers .................. | A61B 18/12 604/114 |
| 5,904,681 A | 5/1999 | West, Jr. | |
| 5,913,854 A | 6/1999 | Maguire | |
| 5,916,150 A | 6/1999 | Sillman | |
| 5,916,213 A | 6/1999 | Haissaguerre | |
| 5,921,982 A | 7/1999 | Lesh | |
| 5,925,045 A | 7/1999 | Reimels | |
| 5,927,284 A | 7/1999 | Borst | |
| 5,928,191 A | 7/1999 | Houser | |
| 5,935,123 A | 8/1999 | Edwards | |
| 5,941,876 A | 8/1999 | Nardella | |
| 5,944,715 A | 8/1999 | Goble | |
| 5,957,881 A | 9/1999 | Peters | |
| 5,957,919 A | 9/1999 | Laufer | |
| 5,971,980 A | 10/1999 | Sherman | |
| 5,971,983 A | 10/1999 | Lesh | |
| 5,980,516 A | 11/1999 | Mulier | |
| 5,989,248 A | 11/1999 | Tu | |
| 5,993,412 A | 11/1999 | Deily | |
| 6,004,316 A | 12/1999 | Laufer | |
| 6,004,319 A | 12/1999 | Goble | |
| 6,010,476 A | 1/2000 | Saadat | |
| 6,010,500 A | 1/2000 | Sherman | |
| 6,012,457 A | 1/2000 | Lesh | |
| 6,015,391 A | 1/2000 | Rishton | |
| 6,024,733 A | 2/2000 | Eggers | |
| 6,042,556 A | 3/2000 | Beach | |
| 6,042,593 A | 3/2000 | Storz | |
| 6,053,923 A | 4/2000 | Veca | |
| 6,063,081 A | 5/2000 | Mulier | |
| 6,071,279 A | 6/2000 | Whayne | |
| 6,074,386 A | 6/2000 | Goble | |
| 6,088,894 A | 7/2000 | Oakley | |
| 6,096,037 A | 8/2000 | Mulier | |
| 6,117,101 A | 9/2000 | Diederich | |
| 6,142,993 A | 11/2000 | Whayne | |
| 6,142,994 A | 11/2000 | Swanson | |
| 6,152,920 A | 11/2000 | Thompson | |
| 6,152,941 A | 11/2000 | Himes | |
| 6,161,543 A | 12/2000 | Cox | |
| 6,165,174 A | 12/2000 | Jacobs | |

(56) References Cited

U.S. PATENT DOCUMENTS

| | | |
|---|---|---|
| 6,193,715 B1 | 2/2001 | Wrublewski |
| 6,197,024 B1 | 3/2001 | Sullivan |
| 6,214,003 B1 | 4/2001 | Morgan |
| 6,217,528 B1 | 4/2001 | Koblish |
| 6,217,576 B1 | 4/2001 | Tu |
| 6,217,598 B1 | 4/2001 | Berman |
| 6,221,088 B1 | 4/2001 | Bays |
| 6,224,592 B1 | 5/2001 | Eggers |
| 6,231,518 B1 | 5/2001 | Grabek |
| 6,235,024 B1 | 5/2001 | Tu |
| 6,237,605 B1 | 5/2001 | Vaska |
| 6,238,347 B1 | 5/2001 | Nix |
| 6,238,393 B1 | 5/2001 | Mulier |
| 6,245,061 B1 | 6/2001 | Panescu |
| 6,245,064 B1 | 6/2001 | Lesh |
| 6,245,065 B1 | 6/2001 | Panescu |
| 6,246,638 B1 | 6/2001 | Zook |
| 6,251,092 B1 | 6/2001 | Qin |
| 6,251,128 B1 | 6/2001 | Knopp |
| 6,270,471 B1 | 8/2001 | Hechel |
| 6,292,689 B1 | 9/2001 | Wallace |
| 6,293,943 B1 | 9/2001 | Panescu |
| 6,293,957 B1 | 9/2001 | Peters |
| 6,296,638 B1 | 10/2001 | Davison |
| 6,325,797 B1 | 12/2001 | Stewart |
| 6,328,736 B1 | 12/2001 | Mulier |
| 6,332,881 B1 | 12/2001 | Carner |
| 6,358,248 B1 | 3/2002 | Mulier |
| 6,361,531 B1 | 3/2002 | Hissong |
| 6,364,876 B1 | 4/2002 | Erb |
| 6,368,275 B1 | 4/2002 | Sliwa |
| 6,383,151 B1 | 5/2002 | Diederich |
| 6,385,472 B1 | 5/2002 | Hall |
| 6,398,792 B1 | 6/2002 | O'Connor |
| 6,409,722 B1 | 6/2002 | Hoey |
| 6,413,254 B1 | 7/2002 | Hissong |
| 6,419,648 B1 | 7/2002 | Vitek |
| 6,425,867 B1 | 7/2002 | Vaezy |
| 6,430,426 B2 | 8/2002 | Avitall |
| 6,440,130 B1 | 8/2002 | Mulier |
| 6,443,952 B1 | 9/2002 | Mulier |
| 6,454,782 B1 | 9/2002 | Schwemberger |
| 6,461,357 B1 | 10/2002 | Sharkey |
| 6,471,697 B1 | 10/2002 | Lesh |
| 6,471,698 B1 | 10/2002 | Edwards |
| 6,474,340 B1 | 11/2002 | Vaska |
| 6,475,216 B2 | 11/2002 | Mulier |
| 6,477,396 B1 | 11/2002 | Mest |
| 6,484,727 B1 | 11/2002 | Vaska |
| 6,488,678 B2 | 12/2002 | Sherman |
| 6,488,680 B1 | 12/2002 | Francischelli |
| 6,494,892 B1 | 12/2002 | Ireland |
| 6,502,575 B1 | 1/2003 | Jacobs |
| 6,503,263 B2 | 1/2003 | Adams |
| 6,514,250 B1 | 2/2003 | Jahns |
| 6,527,767 B2 | 3/2003 | Wang |
| 6,537,248 B2 | 3/2003 | Mulier |
| 6,537,272 B2 | 3/2003 | Christopherson |
| 6,558,382 B2 | 5/2003 | Jahns |
| 6,558,385 B1 | 5/2003 | McClurken |
| 6,565,560 B1 | 5/2003 | Goble |
| 6,565,561 B1 | 5/2003 | Goble |
| 6,584,360 B2 | 6/2003 | Francischelli |
| 6,585,732 B2 | 7/2003 | Mulier |
| 6,605,084 B2 | 8/2003 | Acker |
| 6,610,055 B1 | 8/2003 | Swanson |
| 6,610,059 B1 | 8/2003 | West, Jr. |
| 6,610,060 B2 | 8/2003 | Mulier |
| 6,613,048 B2 | 9/2003 | Mulier |
| 6,645,199 B1 | 11/2003 | Jenkins |
| 6,648,883 B2 | 11/2003 | Francischelli |
| 6,656,175 B2 | 12/2003 | Francischelli |
| 6,663,627 B2 | 12/2003 | Francischelli |
| 6,663,628 B2 * | 12/2003 | Peters ............. A61B 17/32002 606/170 |
| 6,689,131 B2 | 2/2004 | McClurken |
| 6,699,240 B2 | 3/2004 | Francischelli |
| 6,702,810 B2 | 3/2004 | McClurken |
| 6,702,811 B2 | 3/2004 | Stewart |
| 6,706,038 B2 | 3/2004 | Francischelli |
| 6,706,039 B2 | 3/2004 | Mulier |
| 6,716,211 B2 | 4/2004 | Mulier |
| 6,716,215 B1 | 4/2004 | David |
| 6,736,810 B2 | 5/2004 | Hoey |
| 6,752,816 B2 | 6/2004 | Culp |
| 6,755,827 B2 | 6/2004 | Mulier |
| 6,764,487 B2 | 7/2004 | Mulier |
| 6,773,433 B2 | 8/2004 | Stewart |
| 6,776,780 B2 | 8/2004 | Mulier |
| 6,780,180 B1 | 8/2004 | Goble |
| 6,807,968 B2 | 10/2004 | Francischelli |
| 6,824,550 B1 | 11/2004 | Noriega |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart |
| 6,911,019 B2 | 6/2005 | Mulier |
| 6,916,318 B2 | 7/2005 | Francischelli |
| 6,923,803 B2 | 8/2005 | Goble |
| 6,936,046 B2 | 8/2005 | Hissong |
| 6,949,097 B2 | 9/2005 | Stewart |
| 6,949,098 B2 | 9/2005 | Mulier |
| 6,953,461 B2 | 10/2005 | McClurken |
| 6,960,205 B2 | 11/2005 | Jahns |
| 6,962,589 B2 | 11/2005 | Mulier |
| 6,979,332 B2 | 12/2005 | Adams |
| 7,052,494 B2 | 5/2006 | Goble |
| 7,115,139 B2 | 10/2006 | McClurken |
| 7,150,747 B1 | 12/2006 | McDonald |
| 7,166,103 B2 | 1/2007 | Carmel |
| 7,179,255 B2 | 2/2007 | Lettice |
| 7,229,437 B2 | 6/2007 | Johnson |
| 7,232,440 B2 | 6/2007 | Dumbauld |
| 7,237,990 B2 | 7/2007 | Deng |
| 7,247,155 B2 | 7/2007 | Hoey |
| 7,247,161 B2 | 7/2007 | Johnston |
| 7,261,711 B2 | 8/2007 | Mulier |
| 7,276,074 B2 | 10/2007 | Adams |
| 7,278,994 B2 | 10/2007 | Goble |
| 7,309,325 B2 | 12/2007 | Mulier |
| 7,311,708 B2 | 12/2007 | McClurken |
| 7,322,974 B2 | 1/2008 | Swoyer |
| 7,361,175 B2 | 4/2008 | Suslov |
| 7,364,579 B2 | 4/2008 | Mulier |
| 7,416,539 B2 | 8/2008 | Johnston |
| 7,442,191 B2 | 10/2008 | Hovda |
| 7,537,595 B2 | 5/2009 | McClurken |
| 7,604,635 B2 | 10/2009 | McClurken |
| 7,608,072 B2 | 10/2009 | Swanson |
| 7,645,277 B2 | 1/2010 | McClurken |
| 7,651,494 B2 | 1/2010 | McClurken |
| 7,674,263 B2 * | 3/2010 | Ryan ............... A61B 18/148 606/180 |
| 7,691,050 B2 | 4/2010 | Gellman |
| 7,699,846 B2 * | 4/2010 | Ryan ............... A61B 17/32002 606/170 |
| 7,736,361 B2 | 6/2010 | Palanker |
| 7,749,608 B2 | 7/2010 | Laude |
| 7,785,337 B2 | 8/2010 | Adams |
| 7,811,282 B2 | 10/2010 | McClurken |
| 7,815,634 B2 | 10/2010 | McClurken |
| 7,854,736 B2 | 12/2010 | Ryan |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley |
| 7,998,140 B2 | 8/2011 | McClurken |
| 8,012,153 B2 | 9/2011 | Woloszko |
| 8,034,071 B2 | 10/2011 | Scribner |
| 8,038,670 B2 | 10/2011 | McClurken |
| 8,048,070 B2 | 11/2011 | O'Brien |
| 8,083,736 B2 | 12/2011 | McClurken |

(56) References Cited

U.S. PATENT DOCUMENTS

| | | |
|---|---|---|
| 8,105,323 B2 | 1/2012 | Buysse |
| 8,109,956 B2 | 2/2012 | Shadeck |
| 8,172,828 B2 | 5/2012 | Chang |
| 8,177,783 B2 | 5/2012 | Davison |
| 8,202,288 B2 | 6/2012 | Adams |
| 8,216,233 B2 | 7/2012 | McClurken |
| 8,277,474 B2 | 10/2012 | Norman et al. |
| 8,317,786 B2 | 11/2012 | Dahla |
| 8,323,276 B2 | 12/2012 | Palanker |
| 8,348,946 B2 | 1/2013 | McClurken |
| 8,361,068 B2 | 1/2013 | McClurken |
| 8,377,086 B2 | 2/2013 | Flynn |
| 8,388,642 B2 | 3/2013 | Muni |
| 8,414,572 B2 | 4/2013 | Davison |
| 8,568,419 B2 | 10/2013 | de Wekker |
| 9,226,792 B2 | 1/2016 | Bloom |
| 2001/0047183 A1 | 11/2001 | Privitera |
| 2002/0038129 A1 | 3/2002 | Peters |
| 2002/0049483 A1 | 4/2002 | Knowlton |
| 2002/0062131 A1 | 5/2002 | Gallo |
| 2002/0082643 A1 | 6/2002 | Milla |
| 2002/0165549 A1 | 11/2002 | Owusu Akyaw |
| 2003/0014050 A1 | 1/2003 | Sharkey |
| 2003/0032954 A1 | 2/2003 | Carranza |
| 2003/0045872 A1 | 3/2003 | Jacobs |
| 2003/0073993 A1 | 4/2003 | Ciarrocca |
| 2003/0097129 A1 | 5/2003 | Davison |
| 2003/0144656 A1 | 7/2003 | Ocel |
| 2003/0165794 A1 | 9/2003 | Matoba |
| 2003/0191462 A1 | 10/2003 | Jacobs |
| 2003/0204185 A1 | 10/2003 | Sherman |
| 2003/0216724 A1 | 11/2003 | Jahns |
| 2004/0010258 A1 | 1/2004 | Carusillo |
| 2004/0015106 A1 | 1/2004 | Coleman |
| 2004/0015219 A1 | 1/2004 | Francischelli |
| 2004/0024395 A1 | 2/2004 | Ellman |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart |
| 2004/0087940 A1 | 5/2004 | Jahns |
| 2004/0092926 A1 | 5/2004 | Hoey |
| 2004/0111136 A1 | 6/2004 | Sharkey |
| 2004/0111137 A1 | 6/2004 | Shankey |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0167427 A1 | 8/2004 | Quick |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0243163 A1 | 12/2004 | Casiano |
| 2004/0267326 A1 | 12/2004 | Ocel |
| 2005/0010095 A1 | 1/2005 | Stewart |
| 2005/0033280 A1 | 2/2005 | Francischelli |
| 2005/0090815 A1 | 4/2005 | Francischelli |
| 2005/0090816 A1 | 4/2005 | McClurken |
| 2005/0143729 A1 | 6/2005 | Francischelli |
| 2005/0165392 A1 | 7/2005 | Francischelli |
| 2005/0171525 A1 | 8/2005 | Rioux |
| 2005/0209564 A1 | 9/2005 | Bonner |
| 2005/0222566 A1 | 10/2005 | Nakahira |
| 2005/0267454 A1 | 12/2005 | Hissong |
| 2005/0277970 A1 | 12/2005 | Norman |
| 2006/0009756 A1 | 1/2006 | Francischelli |
| 2006/0009759 A1 | 1/2006 | Christian |
| 2006/0064085 A1 | 3/2006 | Schechter |
| 2006/0106375 A1 | 5/2006 | Werneth |
| 2006/0200123 A1 | 9/2006 | Ryan |
| 2006/0259055 A1 | 11/2006 | Thorne |
| 2007/0049920 A1 | 3/2007 | McClurken |
| 2007/0093808 A1 | 4/2007 | Mulier |
| 2007/0100336 A1 | 5/2007 | McFarlin et al. |
| 2007/0118114 A1 | 5/2007 | Miller |
| 2007/0149965 A1 | 6/2007 | Gallo |
| 2007/0179495 A1 | 8/2007 | Mitchell |
| 2007/0208332 A1 | 9/2007 | Mulier |
| 2008/0015563 A1 | 1/2008 | Hoey |
| 2008/0058796 A1 | 3/2008 | O'Brien |
| 2008/0071270 A1 | 3/2008 | Desinger |
| 2008/0207028 A1 | 8/2008 | Schutz |
| 2008/0262489 A1 | 10/2008 | Steinke |
| 2009/0118729 A1 | 5/2009 | Auth |
| 2009/0264879 A1 | 10/2009 | McClurken |
| 2009/0270896 A1 | 10/2009 | Sullivan |
| 2009/0306655 A1 | 12/2009 | Stangenes |
| 2010/0087812 A1 | 4/2010 | Davison |
| 2010/0100095 A1 | 4/2010 | McClurken |
| 2010/0160906 A1 | 6/2010 | Jarrard |
| 2010/0241178 A1 | 9/2010 | Tilson |
| 2010/0298763 A1 | 11/2010 | Adams |
| 2010/0317998 A1 | 12/2010 | Hibner |
| 2011/0009856 A1 | 1/2011 | Jorgensen |
| 2011/0017801 A1 | 1/2011 | Zemlok |
| 2011/0028965 A1 | 2/2011 | McClurken |
| 2011/0066142 A1 | 3/2011 | Tal |
| 2011/0137298 A1 | 6/2011 | Nguyen |
| 2011/0017851 A1 | 7/2011 | Lunde et al. |
| 2011/0196367 A1 | 8/2011 | Gallo |
| 2011/0295249 A1 | 12/2011 | Bloom |
| 2011/0301578 A1 | 12/2011 | Muniz-Medina |
| 2011/0319889 A1 | 12/2011 | Conley |
| 2012/0004657 A1 | 1/2012 | Conley |
| 2012/0012638 A1 | 1/2012 | Huang et al. |
| 2012/0071712 A1 | 3/2012 | Manwaring |
| 2012/0101496 A1 | 4/2012 | McClurken |
| 2012/0109130 A1 | 5/2012 | Casey |
| 2012/0116261 A1* | 5/2012 | Mumaw ........... A61B 17/00234 601/2 |
| 2012/0116397 A1 | 5/2012 | Rencher |
| 2012/0143293 A1 | 6/2012 | Mauch |
| 2012/0150165 A1 | 6/2012 | Conley |
| 2012/0157989 A1 | 6/2012 | Stone |
| 2012/0172877 A1 | 7/2012 | Ryan |
| 2012/0179158 A1 | 7/2012 | Stierman |
| 2012/0184983 A1 | 7/2012 | Chang |
| 2012/0191084 A1 | 7/2012 | Davison |
| 2012/0191117 A1 | 7/2012 | Palmer |
| 2012/0215245 A1 | 8/2012 | Palmer |
| 2012/0221035 A1 | 8/2012 | Harvey |
| 2012/0253343 A1 | 10/2012 | McClurken |
| 2012/0330292 A1 | 12/2012 | Shadduck |
| 2013/0004595 A1 | 1/2013 | Bhatia |
| 2013/0053830 A1 | 2/2013 | Edwards |
| 2013/0085498 A1 | 4/2013 | Matusaitis |
| 2013/0331833 A1* | 12/2013 | Bloom ................ A61B 18/1445 606/33 |
| 2013/0345704 A1 | 12/2013 | Palmer |
| 2014/0005700 A1 | 1/2014 | Casey |
| 2014/0100567 A1 | 4/2014 | Edwards |
| 2014/0155888 A1 | 6/2014 | Edwards |
| 2014/0155889 A1 | 6/2014 | Edwards |
| 2014/0155923 A1 | 6/2014 | Edwards |
| 2014/0276808 A1* | 9/2014 | Gittard ................ A61B 18/1492 606/46 |
| 2014/0277036 A1 | 9/2014 | Flynn |
| 2015/0265337 A1 | 9/2015 | Bloom |
| 2016/0235468 A1 | 8/2016 | Prisco et al. |
| 2016/0235469 A1 | 8/2016 | Prisco et al. |
| 2017/0143406 A1 | 5/2017 | Bloom |

FOREIGN PATENT DOCUMENTS

| | | |
|---|---|---|
| EP | 2133028 | 12/2009 |
| EP | 1853187 | 10/2011 |
| GB | 247060 | 12/2010 |
| WO | WO1996/037156 | 11/1996 |
| WO | WO1997/023169 | 7/1997 |
| WO | WO1998/034550 | 8/1998 |
| WO | WO1998/038932 | 9/1998 |
| WO | WO2003/079911 | 10/2003 |
| WO | WO2011/037664 | 3/2011 |

(56) References Cited

FOREIGN PATENT DOCUMENTS

| WO | WO2012/102838 | 8/2012 |
| WO | 2013191811 | 12/2013 |
| WO | WO2014/084983 | 6/2014 |
| WO | WO2014/133663 | 9/2014 |

OTHER PUBLICATIONS

Non-Final Office Action for U.S. Appl. No. 14/951,697 dated Jul. 12, 2018 (40 pages).
Non-Final Office Action for U.S. Appl. No. 15/046,853 dated Apr. 12, 2018 (39 pages).
International Search Report and Written Opinion dated May 3, 2016 for International Application No. PCT/US2016/018486 (12 pages).

* cited by examiner

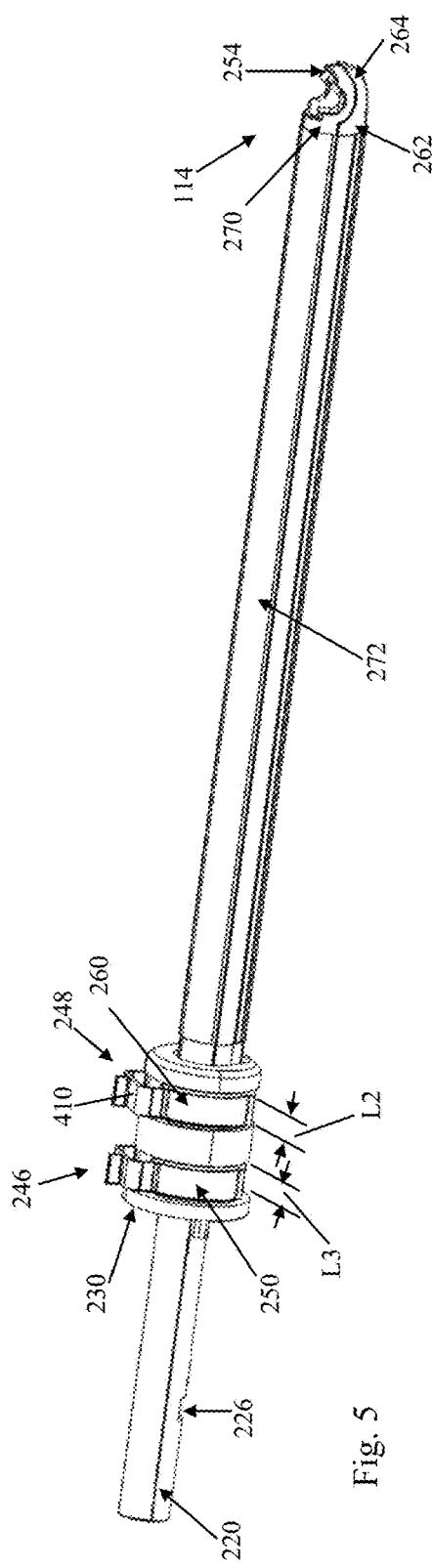
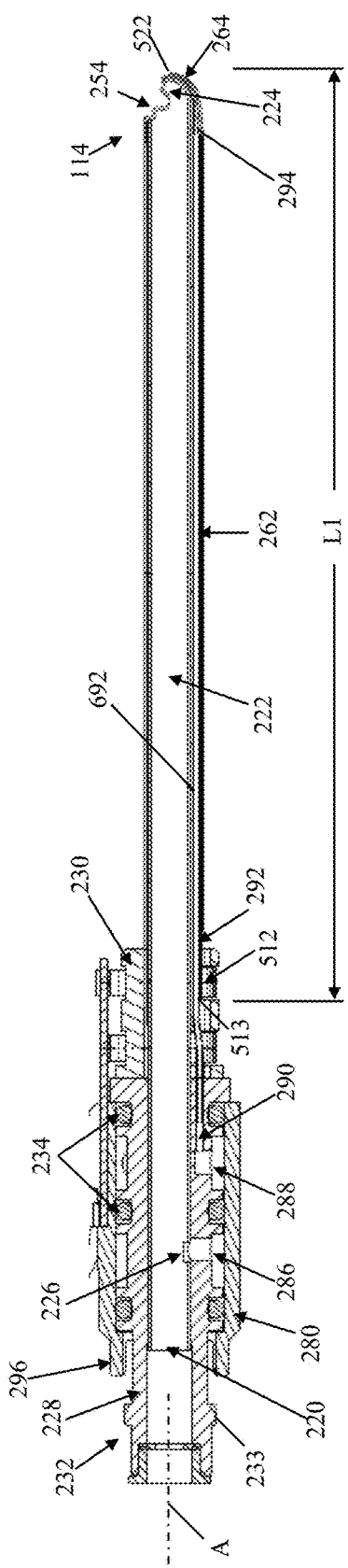
Fig. 5
Fig. 6

ELECTRODE ASSEMBLY FOR RF ENERGY ENABLED TISSUE DEBRIDEMENT DEVICE

CROSS REFERENCE TO RELATED APPLICATIONS

This Non-Provisional Patent Application claims the benefit of the filing date of U.S. Provisional Patent Application Ser. No. 62/117,541, filed Feb. 18, 2015, entitled "ELECTRODE ASSEMBLY FOR RF ENERGY ENABLED TISSUE DEBRIDEMENT DEVICE," which is herein incorporated by reference.

BACKGROUND

This disclosure is generally directed to devices, systems and methods for cutting and sealing tissue such as bone and soft tissue. The concepts presented herein may be particularly suitable for sinus applications and nasopharyngeal/laryngeal procedures and may combine or provide Transcollation® technology with a microdebrider device.

Devices, systems and methods according to the present disclosure may be suitable for a variety of procedures including ear, nose and throat (ENT) procedures, head and neck procedures, otology procedures, including otoneurologic procedures. The present disclosure may be suitable for a varient of other surgical procedures including mastoidectomies and mastoidotomies; nasopharyngeal and laryngeal procedures such as tonsillectomies, trachael procedures, adenoidectomies, laryngeal lesion removal, and polypectomies; for sinus procedures such as polypectomies, septoplasties, removals of septal spurs, anstrostomies, frontal sinus trephination and irrigation, frontal sinus opening, endoscopic DCR, correction of deviated septums and transsphenoidal procedures; rhinoplasty and removal of fatty tissue in the maxillary and mandibular regions of the face.

Sinus surgery is challenging due to its location to sensitive organs such as the eyes and brain, the relatively small size of the anatomy of interest to the surgeon, and the complexity of the typical procedures. Examples of debriders with mechanical cutting components are described in U.S. Pat. Nos. 5,685,838; 5,957,881 and 6,293,957. These devices are particularly successful for powered tissue cutting and removal during sinus surgery, but do not include any mechanism for sealing tissue to reduce the amount of bleeding from the procedure. Sealing tissue is especially desirable during sinus surgery which tends to be a complex and precision oriented practice.

Current approaches to sealing tissue include utilizing Transcollation® technology, where sealing energy is supplied by the Aquamantys® System (available from Medtronic Advanced Energy of Portsmouth, N.H.), which stops bleeding and reduces blood loss during and after surgery. The technology uses a combination of radiofrequency (RF) energy and saline to provide hemostatic sealing of soft tissue and bone, which may lower transfusion rates and reduce the need for other blood management products during or after surgery. Transcollation® technology integrates RF energy and saline to deliver controlled thermal energy to tissue. Coupling of saline and RF energy allows a device temperature to stay in a range which produces a tissue effect without the associated charring found in other ablation methods.

Other devices include both mechanical cutting as well as cauterization or electrocauterization energy. For example, the PK Diego® powered dissector is commercially available from Gyms ENT of Bartlett, Tenn. This device utilizes two mechanical cutting blade components that are moveable relative to each other, one of which acts as an electrode in a bipolar cauterization system. In some instances, this device can exhibit leakage of current along its length, resulting in a potential undesirable situation.

SUMMARY

A bipolar electrosurgical device is disclosed that operates in a mechanical cutting mode and a hemostasis mode. The device includes a housing and a blade assembly extending from the housing. The blade assembly forms a cutting tip and cutting window at a distal end region to provide mechanical cutting of tissue and first and second electrode assemblies to provide electrical energy to tissue. The first electrode assembly includes an outer shaft defining a first electrode surface and the second electrode assembly includes an electrode body extending along and electrically isolated from an outer shaft and defining a U-shape in cross section.

BRIEF DESCRIPTION OF THE DRAWINGS

FIG. 5 is an isometric view of first and second electrode assemblies.

FIG. 6 is a cross section of an irrigation hub and associated irrigation pathways.

DETAILED DESCRIPTION

Figure 1:
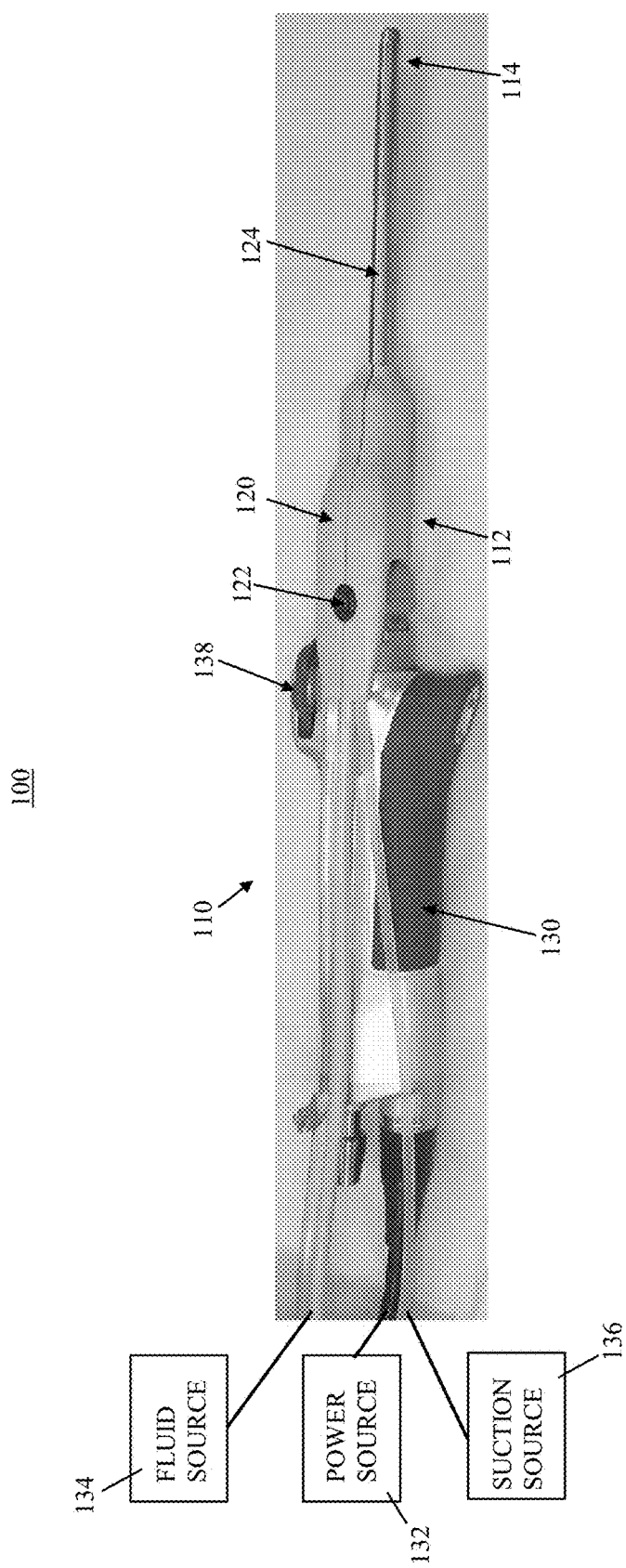
FIG. 1 is a schematic view of a system including a bipolar electrical device.

FIG. 1 illustrates a system 100 that includes a bipolar electrical device 110 having a proximal end region indicated generally at 112 and a distal end region indicated generally at 114. Proximal end region 112 includes a housing 120 maintaining a button 122. A blade assembly 124 extends from the housing to the distal end region 114. As discussed in more detail below, the blade assembly 124 maintains a cutting implement and an electrode assembly to mechanically cut and cauterize or electrocuaterize tissue, respectively.

System 100 further includes a handpiece 130, a power source 132, a fluid source 134 and a suction source 136. It will be appreciated that power source 132, fluid source 134 and suction source 136 can be formed of one or more separate sources as desired and not limited to a single source. Device 110 is configured to couple to handpiece 130, which can be manipulated by a user (e.g., a surgeon) during operation of the system 100 to cut and cauterize or electrocuaterize tissue. In one embodiment, in order to cut tissue, handpiece 130 includes a motor (not shown) internal to the handpiece 130 that is coupled with power source 132. The motor is rotationally coupled with the blade assembly 124 to provide mechanical cutting. The handpiece 130 further includes an actuator 138 external to the handpiece 130 that can be used for manual rotation of one or more components of the device 110 relative to the housing 120 and the handpiece 130.

Power source 132 can further be coupled with the device 110 to deliver electrical energy through blade assembly 124 to the distal region 114. For example, power source 132 can include a generator and optionally may be designed for use with bipolar energy or a bipolar energy supply. For example, the Transcollation® sealing energy supplied by the Aquamantys® System (available from Medtronic Advanced Energy of Portsmouth, N.H.) may be used.

Fluid can be provided to distal region 114 through fluid source 134 connected directly to device 110 and/or to device 110 through handpiece 130. One fluid useful with the present disclosure is saline, however, other fluids are contemplated. Suction source 136 can be coupled to handpiece 130. Use of fluid in conjunction with energy delivery aids in providing optimal tissue effect, thus embodiments of the present disclosure include specific arrangement of the device 110 for coupling of energy with a fluid. In use, a fluid (e.g., saline) may be emitted from an opening at the distal end region 114 of the device 110. Tissue fragments and fluids can be removed from a surgical site through an opening in the distal end region 114 via the suction source 136, as will be further explained below. Both the fluid source 134 and suction source 136 are optional components of system 100.

Figure 2A:
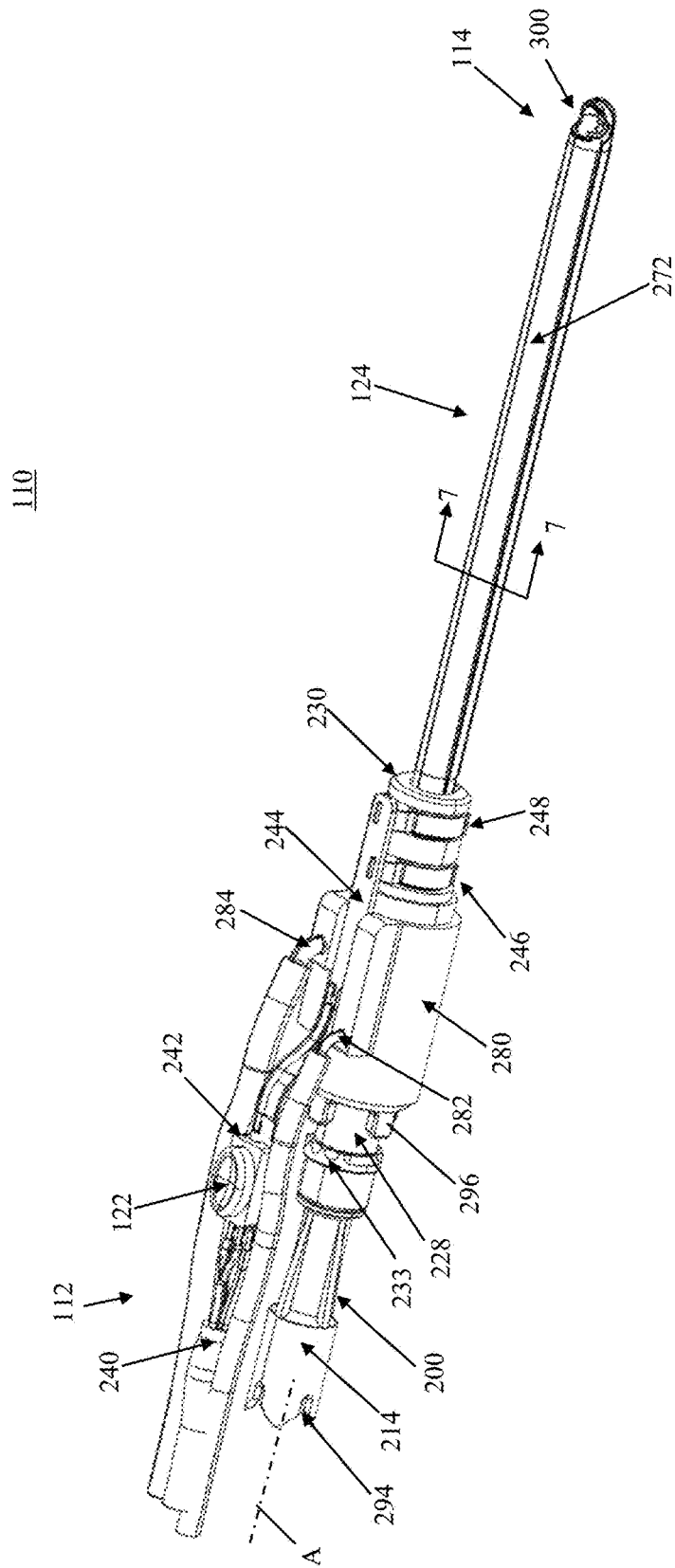
FIG. 2A is an isometric view the bipolar electrical device illustrated in FIG. 1 with a housing removed.
Figure 2B:
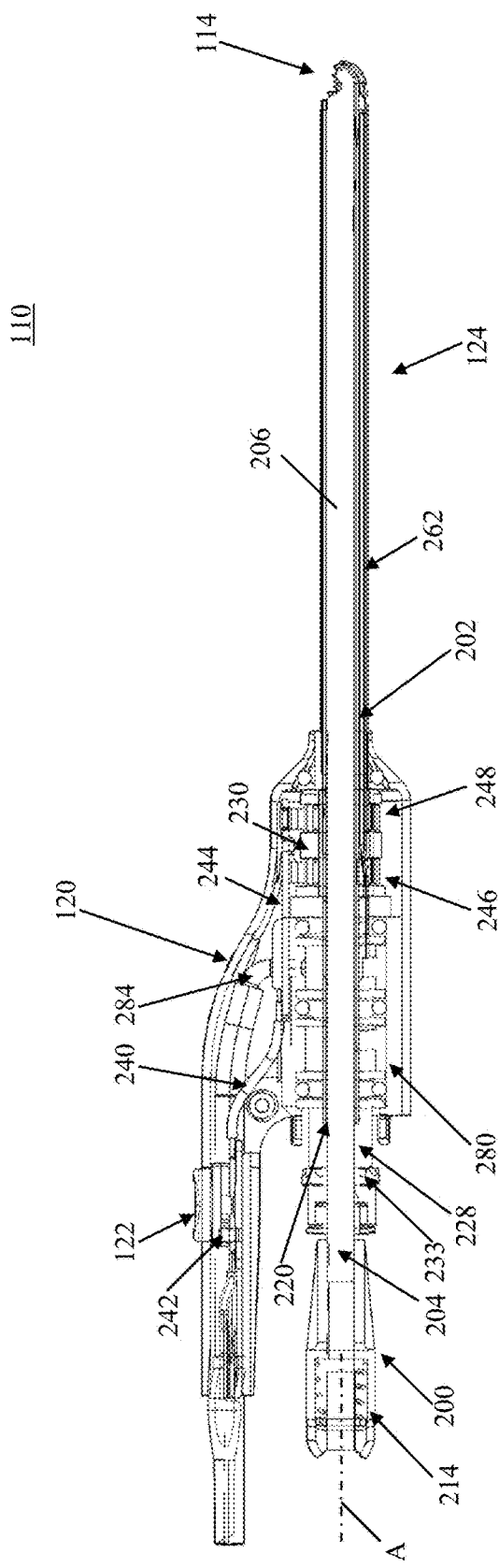
FIG. 2B is a cross sectional view of the bipolar electrical device illustrated in FIG. 1.

With further reference to FIGS. 2A and 2B, an isometric view of device 110 with housing 120 removed and a cross section of device 110 are provided. Details for operation of device 110 are provided below. In general, device 110, and in particular blade assembly 124, includes an inner shaft assembly 200 rotatably disposed within an outer shaft assembly 202. Upon final assembly, the device 110 is operable with the handpiece 130 (FIG. 1) to provide mechanical cutting due to rotation between the inner shaft assembly 200 and the outer shaft assembly 202. Further details of the inner shaft assembly 200 and outer shaft assembly 202 are provided below in relation to FIGS. 3 and 4, respectively. In addition to mechanical cutting, device 110 is operable to provide energy to tissue through a first electrode assembly 246 and a second electrode assembly 248 due to operation of button 122, further described below with respect to FIG. 5. Also during operation, device 110 can provide irrigation to distal end region 114, for example interior to outer shaft assembly 202 and/or exterior to outer shaft assembly 202, as discussed below with respect to FIGS. 6 and 7. Moreover, a user, through operation of actuator 138, can rotate the outer shaft assembly 202 with respect to housing 120 and/or inner shaft assembly 200 so as to alter an orientation of the outer shaft assembly 202 with respect to tissue of interest, as further discussed with respect to FIGS. 8A and 8B. Example rotary electrical connection assemblies allowing orientation of outer shaft assembly 202 to be adjusted are further described in FIGS. 9A-10B.

Figure 3:
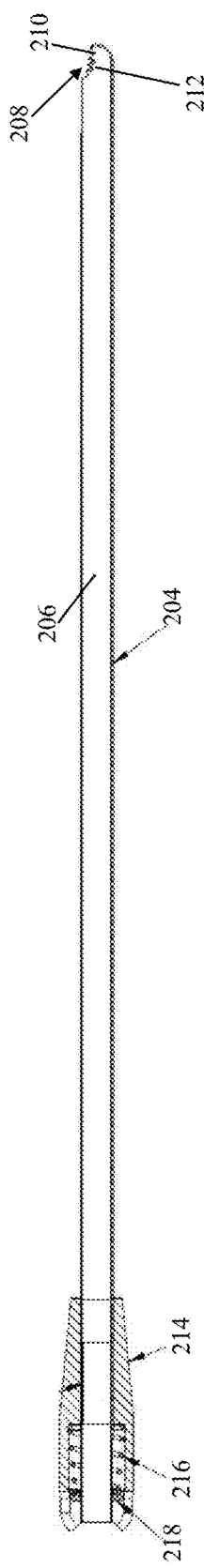
FIG. 3 is a cross sectional view of an inner shaft assembly.

With further reference to the cross section of FIG. 3, the inner shaft assembly 200 includes a first tubular member (also referred to as an inner shaft) 204 defining a lumen 206 and a cutting tip 208. In one embodiment, the cutting tip 208 defines a serrated edge 210 including teeth surrounding an opening 212 that is fluidly connected to the lumen 206. Alternatively, the cutting tip 208 can assume a variety of other forms. In one embodiment, the first tubular member 204 is formed of a rigid material, such as 304 stainless steel, and is linear in longitudinal extension. Alternatively, the first tubular member 204 can be configured to effectuate bending thereof, such as by a flexible coupling (not shown). A hub 214 coupled to the first tubular member 204 is adapted for connection to the motor of the handpiece 130 (FIG. 1). The motor provides rotational power to the inner shaft assembly 200. The inner shaft assembly 200 further includes a biasing member 216 disposed within the hub 214. Upon final assembly, biasing member 216 biases the cutting tip 208 into contact with outer shaft assembly 202. A cap 218 retains the biasing member within the hub 214 and also creates a fluid seal to suction source 136. In one embodiment, lumen 206 is fluidly coupled with suction source 136 (FIG. 1) to provide aspiration of tissue that is cut by the cutting tip 208.

Figure 4:
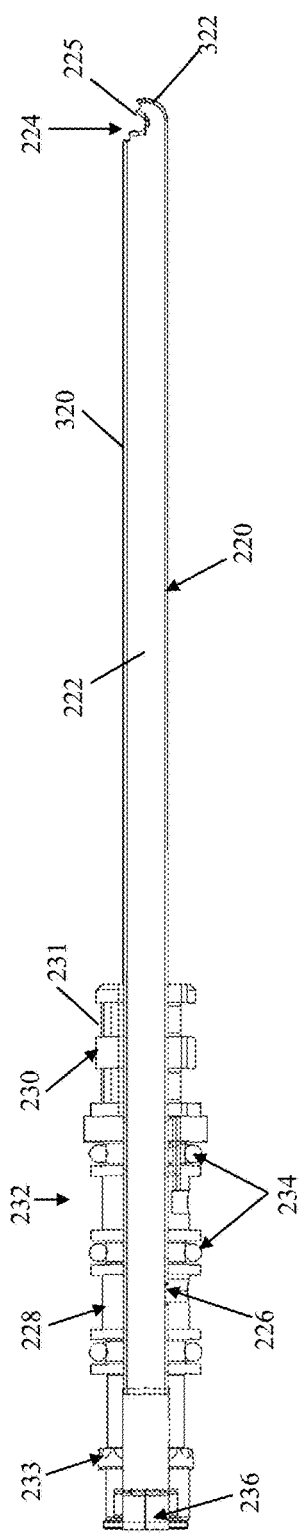
FIG. 4 is a cross section view of an outer shaft assembly.

As illustrated in the cross section of FIG. 4, the outer shaft assembly 202 includes a second tubular member (also referred to as an outer shaft) 220 defining a lumen 222 and a cutting window 224. The cutting window 224, in one embodiment, is defined by a serrated edge 225. In one embodiment, the second tubular member 220 is rigid and longitudinally straight or linear and formed by 304 stainless steel. In alternative embodiments, the second tubular member 220 can incorporate, or be forced to assume, one or more bends. Regardless, the second tubular member 220, and in particular the lumen 222, is sized to co-axially receive the first tubular member 204 in a manner that allows rotation and/or oscillation of the first tubular member 204 relative to second tubular member 220, as well as to provide a path for internal irrigation. To this end, the lumen 222 of the second tubular member 220 has a diameter slightly greater than an outer diameter of a corresponding portion of the first tubular member 204, and defines an irrigation inlet 226 fluidly connected to the lumen 222.

A first, proximal hub member 228 and a second, distal hub member 230 form a hub assembly 232. The hub assembly 232, including the first hub member 228 and the second hub member 230, are connected to tubular member 220 in a fixed manner so as to rotate together. As such, rotation of the hub assembly 232 causes rotation of the cutting window 224. The hub assembly 232 is adapted for connection to the actuator 138 (FIG. 1) in order to rotate the outer shaft assembly 202, and thus the cutting window 224, relative to the housing 120 (FIG. 1) and the inner shaft assembly 200. In particular, the hub 228 can include an engagement member 233 (e.g., gear teeth) that directly couples with a drive member (e.g., a gear) of the actuator 138 to effectuate rotation of hub 228 and, due to the fixed coupling with hub assembly 232 and tubular member 220, the cutting window 224. A plurality of o-rings 234 are coupled to the first hub member 228 to provide seals for the first hub member 226, as discussed below. In addition, a cap 236 is provided at a proximal end of the outer shaft assembly 202.

Returning to FIGS. 2A and 2B, device 110 further includes wiring 240 electrically connected with power source 132 (FIG. 1). Wiring 240 extends to a switching element 242 that controls flow of electrical energy between the wiring 240 and a printed circuit board (PCB) 244 upon operation of button 122. The PCB 244 is coupled with first and second electrode assemblies 246 and 248. The electrode assemblies 246 and 248 are electrically isolated from one another so as to provide bipolar electrical energy delivery to tissue positioned proximate the distal region 114.

As illustrated in FIG. 5, the first electrode assembly 246 includes a first rotary electrical connection assembly 250 maintained by second hub member 230, second tubular member 220 (forming a first elongate electrode body) and a first electrode 254 positioned at distal end region 114 of the device 110. First electrode 254 forms an electrode surface at a distal end 314 of the first elongate electrode body 220. In a similar manner, the second electrode assembly 248 includes a second rotary electrical connection assembly 260 maintained by second hub member 230, a second elongate electrode body 262 and a second electrode 264 positioned at distal end region 114 of device 110. Second electrode 264 forms an electrode surface at a distal end 514 of the second elongate electrode body 262.

Electrodes (i.e., electrode surfaces) 254 and 264 comprise bipolar electrodes and may comprise wet or dry electrodes. Electrodes 254 and 264 may be used to deliver any suitable energy for purposes of coagulation, hemostasis or sealing of tissue. Electrode surfaces 254, 264 can be spaced apart such that, when brought in close proximity or contacting tissue and upon activation of button 122, provide energy delivery to tissue. The insulating coating 270 is applied to second tubular member 220 to electrically isolate second tubular member 220 from electrode body 262. In addition, an insulating layer 272 (e.g., formed from through a heat shrinking process) can be applied around electrode body 262.

With reference to FIGS. 2A, 2B and 6, electrodes 254 and 264 are particularly useful with fluid such as saline provided by fluid source 134 (FIG. 1) which may be emitted at distal end region 114. In order to provide fluid delivery to distal end region 114, device 110 includes an irrigation hub 280. As illustrated in FIG. 2A, irrigation hub 280 includes a first fluid connector 282 and a second fluid connector 284.

First fluid connector 282 is fluidly coupled with a first annular channel 286 formed in first hub member 228. First annular channel 286 is fluidly coupled with irrigation inlet 226. Fluid entering inlet 226 is carried within lumen 222 between first tubular member 204 and second tubular member 220. Fluid carried within lumen 222 is dispensed through cutting window 224.

Second fluid connector 284 is fluidly coupled with a second annular channel 288 formed in first hub member 228. Second annular channel 288 is fluidly coupled with a passageway 290 disposed within the first hub member 228 and connected with the tubing 292 positioned between second tubular member 220 and electrode body 262. Tubing 292 forms an irrigation channel 692 and terminates at an outlet 294 proximal the electrodes 254 and 264.

As illustrated, the second elongate electrode body 262 is formed of a rigid material, such as silver, 304 stainless steel or other conductive material, and is linear in longitudinal extension. Alternatively, the second elongate electrode body 262 can be configured to effectuate bending thereof and can be configured to bend in like manner and contemporaneously with the first elongate electrode body 220. In any event, the second elongate electrode body 262 extends a length L1 in a direction parallel to central axis A of inner shaft 200, along an outer circumference 320 of the outer shaft 202. The length L1 is defined by a distance between a proximal edge 513 at a proximal end 512 of the electrode body 262 and a distal-most tip 522 of the electrode body 262.

In the illustrative embodiment, distal end 514 of the electrode body 262 terminates at a position proximate the distal end region 114. The proximal end 512 of the electrode body 262 terminates within and is coupled to hub member 230 such that upon rotation of hub assembly 232, electrode body 262 rotates with the outer shaft assembly 202 about central axis A. Proximal end 512 is electrically coupled to rotary electrical connection assembly 260. The orientation of tubular member 220, when coupled with electrode body 262, is such that the cutting window 224 of the tubular member 220 faces in a direction opposite the electrode body 262. In this way, the serrated edge 225 of the cutting window 224 is fully exposed, as shown, relative to the electrode body 262.

Figure 7:
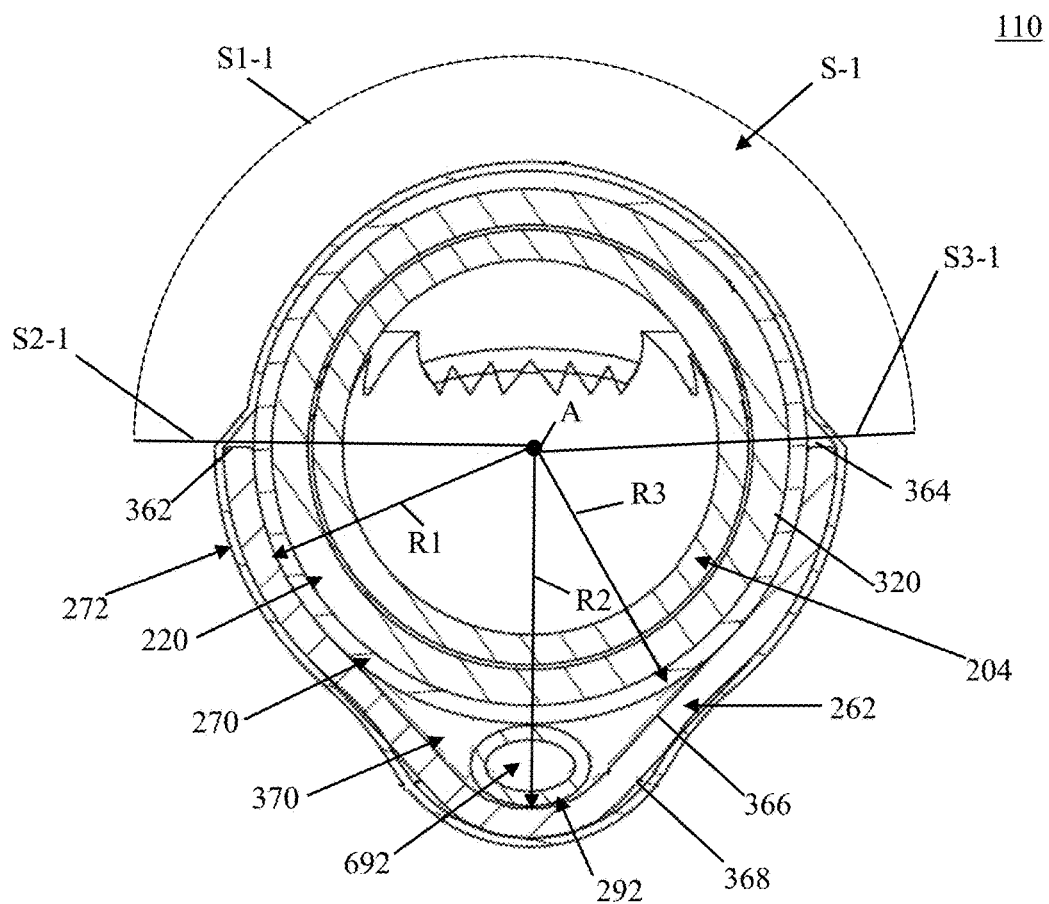
FIG. 7 is a cross section of the bipolar electrical device taken along line 7-7 of FIG. 2A.

FIG. 7 is a cross sectional view taken along line 7-7 in FIG. 2A, showing a configuration of tubular members 204, 220, electrode body 262, insulating coating 270, insulating coating 272 and tubing 292. The electrode body 262 is U-shaped, adjoining with the insulating coating 270 on either side of the tubing 292 and encompassing the tubing 292. Tubing 292 is elliptical in cross section, but can be formed of other cross sectional shapes as well (e.g., a circle).

The second elongate electrode body 262 defines an arcuate shape in cross section with respect to a plane that is perpendicular to the central axis A. The arcuate shape of the electrode body 262 is defined by opposed, spaced apart, first and second ends 362, 364, an inner arcuate surface 366 facing the tubular member 220 and an outer arcuate surface 368 opposite the inner surface 366. Since opposed first and second ends 362, 364 of the electrode body 262 are spaced apart, the electrode body 262 forms less than a full tubular member in cross section. In this manner, opposed ends 362, 364 and inner surface 366 form a partial lumen defining a trench 370. The trench 370 is sized to co-axially receive the tubular member 220 therein such that the inner surface 366 partially surrounds the outer circumference 320 of tubular member 220. To this end, a first radius R1 of the trench 370 is sized to accommodate the outer circumference 320 of tubular member 220 having an insulating coating 270 thereon. In other words, radius R1 is slightly greater than an outer radius R3 of insulating coating 270, where the outer radius R3 is measured from the central axis A to an outer surface of the insulating coating 270. The trench 370 may include a second radius R2, greater than radius R1 to allow for irrigation tubing 292 to be positioned between the second tubular member 220 and electrode body 262.

In some embodiments, and as best viewed in FIG. 7, the arcuate shape of electrode body 262 comprises a U-shape in cross section. In some embodiments, the U-shape is defined by opposed ends 362, 364 spaced around the outer circumference 320 less than 180 degrees. In further embodiments, the U-shape may be defined by opposed ends 362, 364 spaced approximately 180 degrees around outer circumference 320 while in still further embodiments, opposed ends 362, 364 are spaced greater than 180 degrees around the outer circumference 320 of outer shaft 202. Regardless, the electrode body 262, when viewed in cross section along an entirety of its length L1 and with respect to the plane that is perpendicular to the central axis A, defines a maximum distance D1 from the central axis A that includes conductive material such that, for a circle C1 having an origin at the central axis A and a circumference at the maximum distance D1, there exists at least one sector S-1 of the circle C1 free of conductive material. In the illustrative embodiment, the sector S-1 is bounded by arc S1-1, and radii S2-1 and S3-1. An electrode body (e.g., 262) formed in this manner may advantageously prevent or reduce electrical leakage along its length in that electrical energy is not required to travel from the proximal end 112 to the distal end 114 of the device 110 along the blade assembly 124 a full 360 degrees in cross section.

Figure 8A:
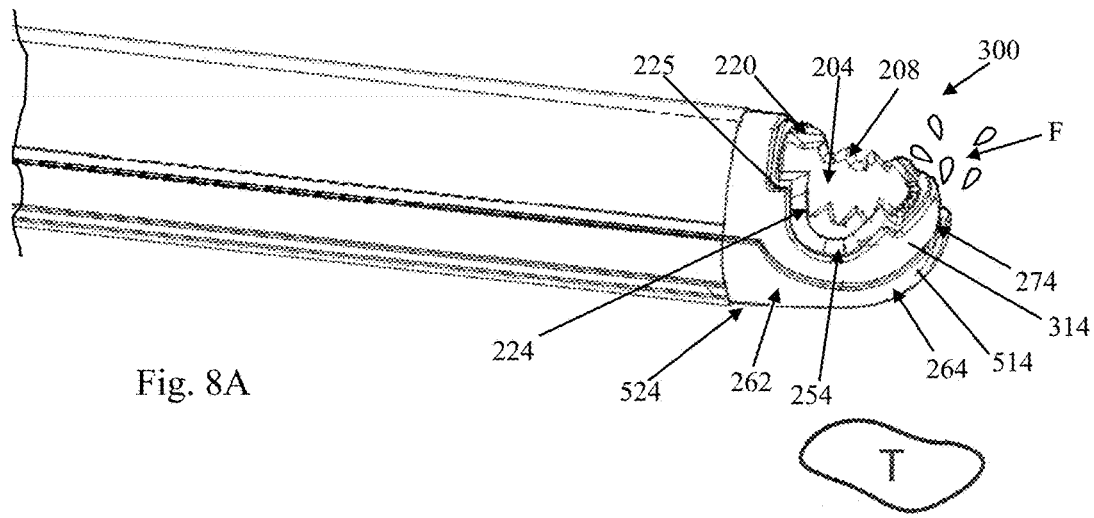
FIGS. 8A and 8B are isometric views of a distal end region of a bipolar electrical device in first and second special orientations, respectively.
Figure 8B:
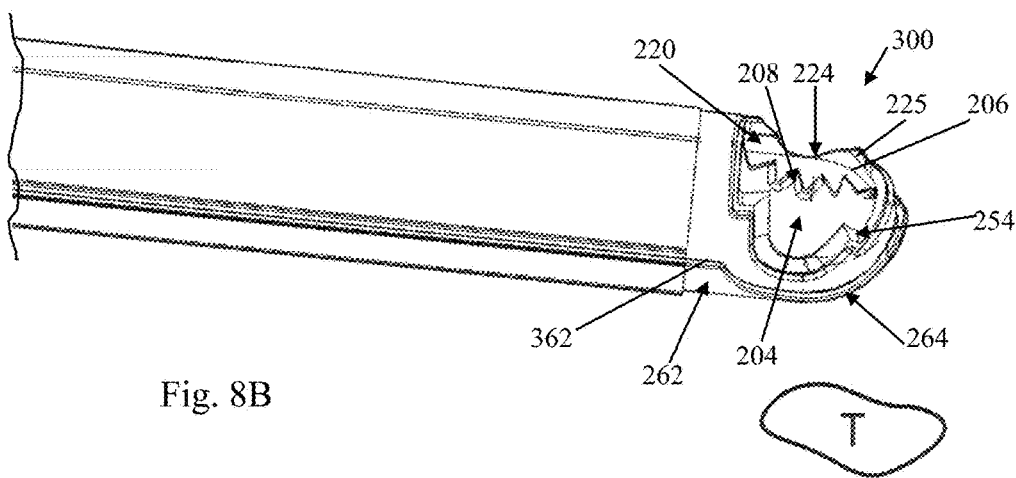

With reference to FIGS. 8A and 8B, the electrode body distal end 514 may comprise a shape that is complementary to the shape of a distal end 314 of tubular member 220 and in this way is shaped to follow a contour of the distal end 314. Stated otherwise, the second elongate electrode body distal end 514 may be sized to receive the outer shaft assembly distal end 314 such that the distal ends (314, 514) of tubular member 220 and second elongate electrode body 262 may be "nested". In some embodiments, and as depicted, the electrode body 262 extends around tubular member 220 to cover a distal-most tip 322 (FIG. 4) of tubular member 220. Advantageously, in this configuration the electrode surfaces 254, 264 can be spaced to provide energy delivery to tissue (e.g., by controlling a distance between electrode surfaces 254, 264). In one embodiment, the electrode surfaces 254 and 264 can be formed to extend along an entire or partial length of the cutting window 224.

In some embodiments, and likewise as shown, the electrode body 262 may form a distal cup 524 fluidly coupled with irrigation channel 692 formed by the tubing 292 that is positioned between the second tubular member 220 and the electrode body 262. The distal cup 524 is configured to direct fluid F from the irrigation channel 692 out a fluid outlet 274 located between the distal cup 524 and the distal end 314 such as depicted in FIG. 8A. In this configuration, the irrigation channel 692 is advantageously situated between and immediately adjacent bipolar electrode surfaces 254, 264 to provide coupling of the electrical energy and fluid F delivered to tissue T. Alternatively, or in addition, as described below, fluid may be provided through cutting window 224.

During operation, and with reference to FIG. 1, device 110 is coupled to handpiece 130 by inserting the proximal end region 112 into an opening (not shown) in the handpiece 130. In particular, the hub 214 is inserted into the opening and can include a proximal engagement member 295 (e.g., including tabs illustrated in FIGS. 2A and 2B) for coupling with the motor of the handpiece 130. Upon insertion of the device 110 into the handpiece 130, actuator 138 engages with the engagement member 233 of hub 228. In one embodiment, the irrigation hub 280 (or other component of device 110) can include one or more alignment tabs 296 that orient the housing 120 with respect to the handpiece 130. In one particular embodiment, the tabs 296 are arranged such that coupling between device 110 and handpiece 130 orients button 122 perpendicular to a rotational axis of actuator 138. In the embodiment illustrated in FIG. 1, a right-handed user will have access to button 122 and actuator 138 through their right index finger. In similar manner, device 110 can be rotated 180 degrees prior to insertion into the handpiece 130 such that button 122 faces an opposite direction to that illustrated in FIG. 1. In this orientation, a left-handed user will have access to button 122 and actuator 138 through their left index finger. Upon final connection with the handpiece 130, device 110 may comprise two modes: a cutting or debridement mode and a sealing or hemostasis mode. These two modes may further be mutually exclusive. In an alternative embodiment, the two modes can be performed simultaneously.

As illustrated in FIGS. 8A and 8B, the cutting tip 208 provided by the first tubular member 204 is selectively exposed at the cutting window 224 relative to tissue site T. Upon final assembly, the cutting tip 208 is positioned at the cutting window 224 with the two components being rotatable relative to one another in oscillation or rotation (or both) in order to mechanically cut tissue (e.g., as driven by a motor contained within the handpiece 130 coupled with the power source 132 of FIG. 1). The cutting tip 208 and the cutting window 224 combine to define a cutting implement 300. Hemostasis is achieved via energy delivery to tissue T through energy delivered to electrodes 254 and 264. In one embodiment, hemostasis is delivered while cutting implement 300 is not active or cutting. In one embodiment, energy may be advantageously delivered simultaneously with a fluid such as saline to achieve an optimal tissue effect by delivering controlled thermal energy to tissue.

By way of explanation, FIG. 8A illustrates the first tubular member 204 rotated to a position whereby the cutting tip 208 is exposed via the cutting window 224 and away from tissue site T. Upon partial rotation of the second tubular member 220 relative to the first tubular member 204 as illustrated in FIG. 8B, or vice-versa, less of the cutting tip 208 is exposed at the cutting window 224 and the orientation of the cutting window 224 approaches the tissue site T. In some positions, the second tubular member 220 and the electrode body are rotated such that the central lumen 206 of the first tubular member 204 is closed relative to the cutting window 224. Regardless, the second tubular member 220 and the electrode body 262 are rotatable with respect to the first tubular member 204 in either direction a full 360 degrees through operation of the actuator 138 (FIG. 1). As such, operation of the actuator 138 can rotate the second tubular member 220 and the electrode body 262 from FIG. 8B to the position of FIG. 8A in either direction as desired so as to face the tissue site T of interest.

Specific surgical techniques facilitated by the surgical cutting instruments described herein can be conducted in connection with features discussed above. During use, a hand (not shown) of a user (not shown) is employed to grasp the handpiece 130 (FIG. 1). In this regard, and in one embodiment, the handpiece 130 forms an exterior contour adapted to ergonomically fit within a user's hand, such as by grasping the handpiece 130. Regardless, the user then deploys the cutting implement 300, manipulating the handpiece 130 to deploy the cutting implement 300 to target site T. Following initial deployment to the target site T, the cutting window 224 has a first spatial orientation relative to the target site as indicated by the orientation of the cutting window 224 relative to target site T. More particularly, with the orientation of FIG. 8A, the cutting window 224 exposes the cutting tip 208. Further, the handpiece 130, can be generally described as defining an upright orientation as illustrated in FIG. 1 when naturally grasped by the user's hand, with the handpiece 130 positioned within the user's palm, such that the actuator 138 is proximate the user's thumb or index finger (not shown). In addition, the button 122 can be in close proximity to actuator 138 such that the user can easily switch back and forth by controlling spatial orientation of cutting window 224 and delivering RF energy through operation of button 122.

An example surgical procedure may then require removal of tissue and/or hemostasis of tissue T in a direction not directly facing or adjacent the cutting window 224. In the orientation of FIG. 8A, the cutting window 224 is away from the tissue site T, requiring movement of the cutting window 224 to allow either the cutting tip 208 or the electrodes 254 and 264 to interact with the tissue T. To accomplish alteration of the spatial orientation of the cutting window 224, and with additional reference to FIG. 8A, the user (not shown) rotates the actuator 138 in a desired direction. In particular, the user's thumb (not shown) and/or index finger (not shown) of the hand that is otherwise grasping the handpiece 130 is used to rotate the actuator 138. Rotation of the actuator 138 is translated to the hub 228. Rotation of the hub 228, in turn, causes the second tubular member 220, and thus the cutting window 224, to rotate relative to the tissue site T, the housing 120, the cutting tip 208 and the handpiece 130. Rotation of the actuator 138 continues until the cutting window 224 assumes the second spatial orientation shown in FIG. 8B. Notably, a rotational orientation of the handpiece 130, need not change when translating the cutting window 224 from the spatial orientation of FIG. 8A to the spatial orientation of FIG. 8B or any other orientation relative to axis A to face the tissue site T. That is to say, the cutting window 224 can be rotated to face any direction about axis A.

Transition of the cutting window 224 from the spatial orientation of FIG. 8A to the spatial orientation of FIG. 8B (or other orientation as desired throughout a full 360 degree rotation about axis A) is accomplished, in one embodiment, with only a single hand of the user. The device 110 is configured such that the cutting window 224 can be spatially rotated relative to the handpiece 130 without requiring both hands of the user to otherwise grasp the handpiece at two discrete locations and apply a twisting or torque-generating motion. In one embodiment, the single-handed cutting window rotation is accomplished by configuring the actuator 138 such that a movement axis of the actuator 138 is off-set from axis A, which is coaxial with a major axis of the hub 228. That is to say, the actuator 138 moves (e.g. rotates) about an axis or plane that is not co-axial with axis A of the hub 228; instead, movement of the actuator 138 is translated into rotation of the hub 228 about the axis A of the second hub 228. In one embodiment, the rotational axis of the actuator 138 is perpendicular to axis A. With this approach, then, the actuator 138 can be located at any desired position relative to the handpiece 130 so as to promote single-handed operation.

During delivery of electrical energy in hemostasis mode, fluid can be provided to distal end region 114 through cutting window 224, outlet 294 (FIG. 6), or both. As described above, fluid delivered to distal end region 114 interacts with electrodes 254 and 264. In this manner, electrodes 254 and 264 can advantageously provide Transcollation® sealing of tissue when used with the Transcollation® sealing energy supplied by the Aquamantys System, available from the Advanced Energy Division of Medtronic, Inc. With respect to "wet" RF coagulation technology, the technology for sealing tissue described in U.S. Pat. Nos. 6,558,385; 6,702,810, 6,953,461; 7,115,139, 7,311,708; 7,537,595; 7,645,277; 7,811,282; 7,998,140; 8,048,070; 8,083,736; and 8,361,068 (the entire contents of each of which is incorporated by reference) describe bipolar coagulation systems believed suitable for use with device 110. Other systems for providing a source of energy are also contemplated.

Figure 9A:
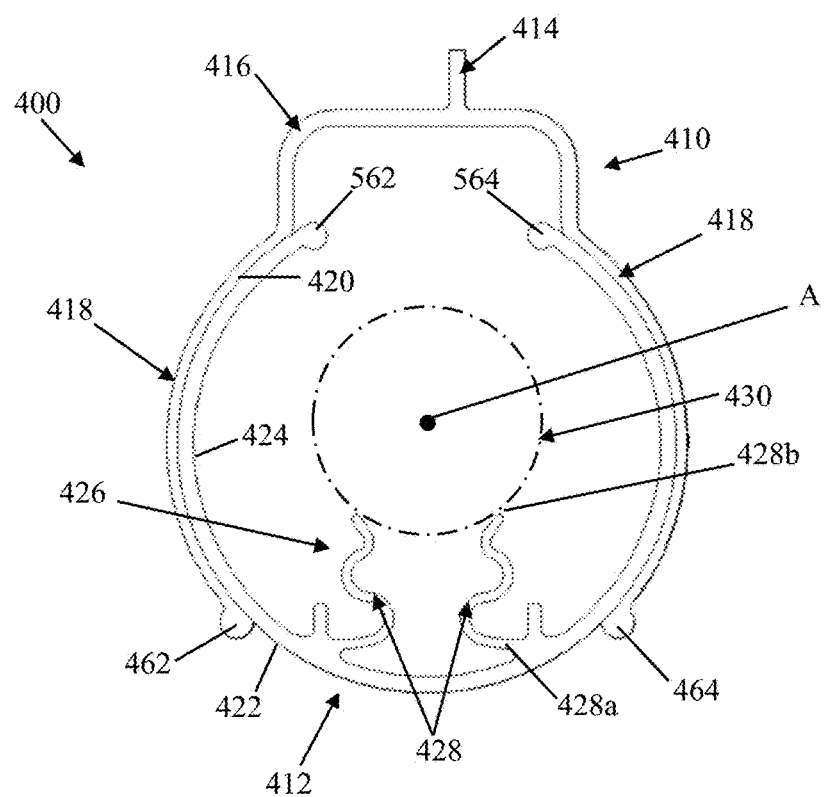
FIGS. 9A and 9B are plan views of first and second rotary electrical connection assemblies, respectively.
Figure 9B:
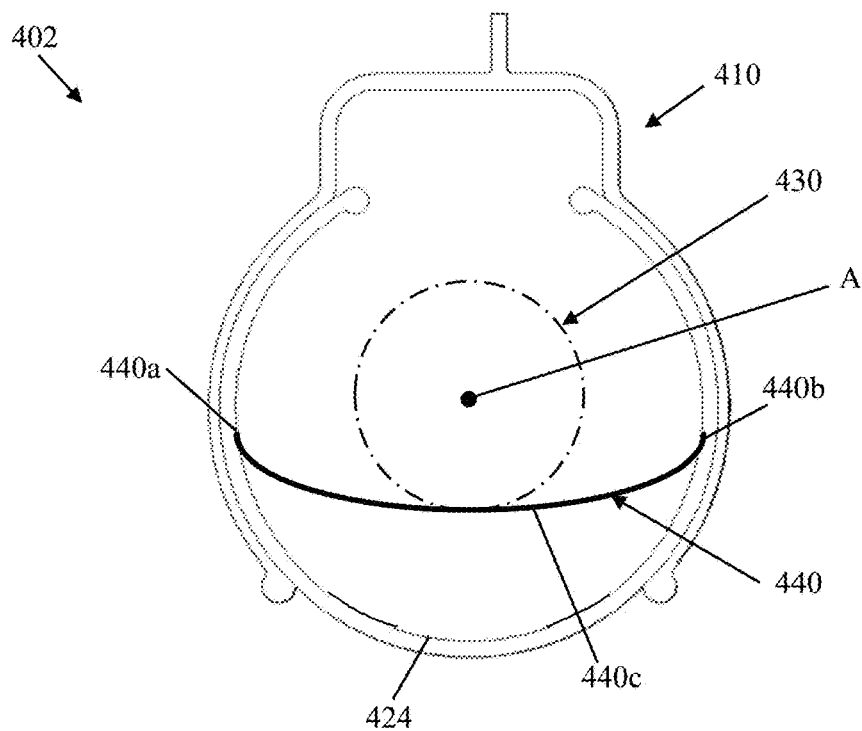

FIGS. 9A and 9B illustrate example rotary electrical connection assemblies 400 and 402, respectively, which allow device 110 to provide 360 degree rotation of the cutting window 224 with respect to housing 120 while still providing electrical energy to the distal region 114. Either of the assemblies 400, 402 can be used as the rotary electrical connection assemblies 250 and 260 discussed with respect to FIG. 5. The structures of assemblies 400, 402, as discussed below, can reduce current leakage compared with other structures. With reference to assembly 400 illustrated in FIG. 9A, the assembly 400 includes an outer, stationary connector 410 and an inner, rotating connector 412. The inner connector 412 is connected to hub 230 to rotate therewith, while outer connector 210 is held stationary upon rotation of hub 230 about axis A. The outer connector 410 and the inner connector 412 can be formed of material exhibiting suitable electrical conductive properties, such as brass. The stationary connector 410, in one embodiment, is a unitary body that includes an extension 414, a bridge 416 coupled with the extension 414 and opposed arcuate arms 418 extending from opposite sides of the bridge 416. The extension 414 is configured to connect to the PCB 244 (FIG. 2). Electrical energy provided to the extension 414 is carried by the bridge 416 to each of the arms 418.

The arms 418 define an inner engagement surface 420 that is in contact with the inner connector 412, in particular an outer, first surface 422 of the inner connector 412. An inner, second surface 424 of the inner connector is opposite first surface 422. An inner extension member 426 extends inwardly toward axis A to connect with an arcuate connecting surface 430. In one example, arcuate surface 430 is second tubular member 220 or electrode body 262. Extension member 426 exhibits resilient properties and defines a natural position and a deflected position in order to engage and capture arcuate surface 430. In the illustrated embodiment, extension member 426 includes a pair of opposed tabs 428 extending from the second surface 424. Each tab 428 includes a first end 428a connected with the second surface 424 and a second end 428b opposite the first end 428a. Upon coupling of the member 426 with the arcuate surface 430, the second ends 428b of each of the tabs 428 deflect away from the rotational axis A. The resilient properties of the extension member 426 maintain contact with the arcuate surface 430 upon final assembly.

Assembly 402 illustrated in FIG. 9B is similar to assembly 400, with similar elements similarly numbered. In contrast to assembly 400 of FIG. 9A, assembly 402 includes an extension member 440 that extends from a first end 440a connected to inner surface 424 to a second end 440b that is connected to inner surface 424 at a different position. An intermediate portion 440c of the extension member 440 transitions from a natural position to a deflected position when coupled with arcuate surface 430. Due to resilient properties of extension member 440, the intermediate portion 440c maintains electrical contact with arcuate surface 430 upon final assembly.

Figure 10B:
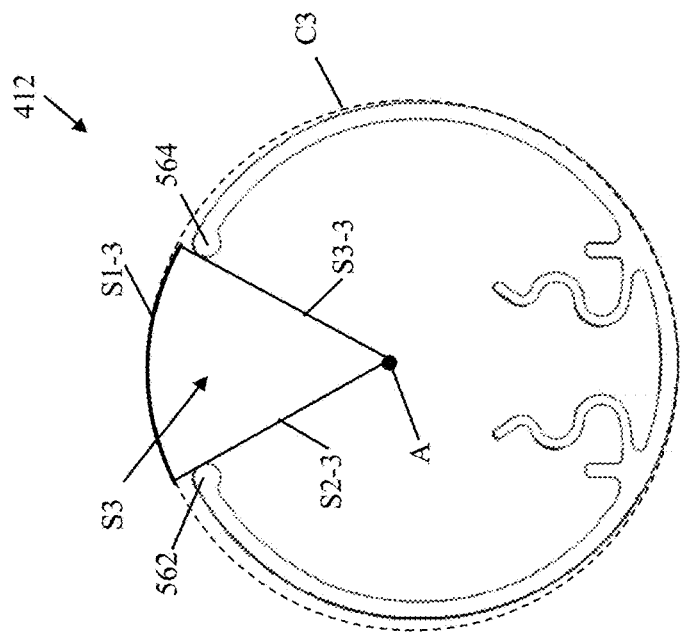
FIGS. 10A and 10B are plan views of an outer connector and an inner connector, respectively.
Figure 10A:
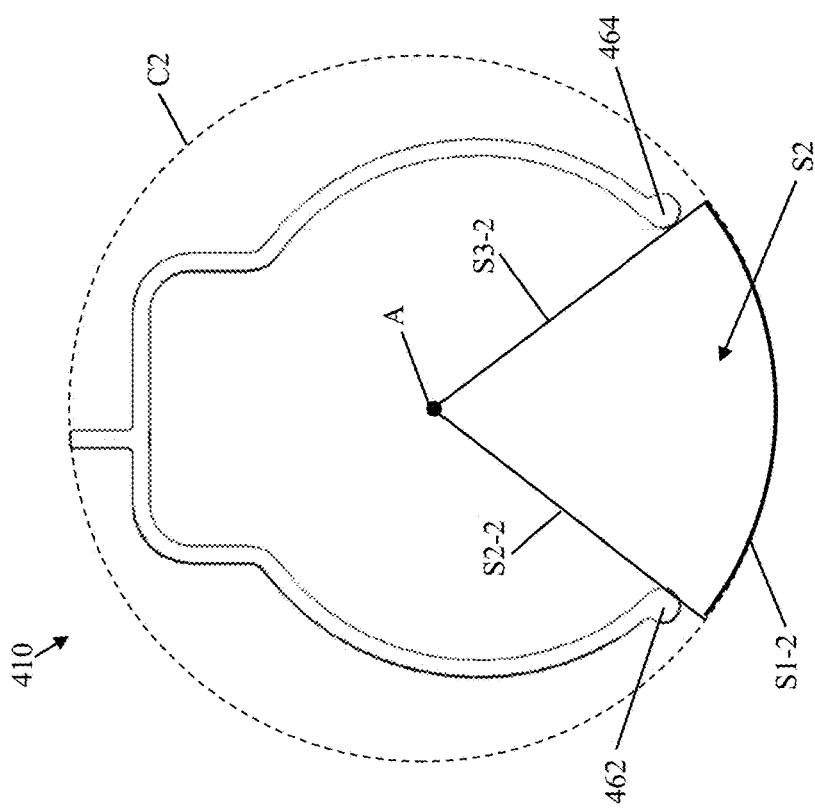

With reference among FIGS. 5, 10A and 10B, the outer, stationary connector 410 extends longitudinally a length L2 (FIG. 5) in a direction parallel to central axis A of inner shaft 200, along the outer, first surface 422 of inner connector 412. In like manner, the inner, rotating connector 412 extends longitudinally a length L3 in a direction parallel to central axis A of inner shaft assembly 200, along an outer surface 231 (FIG. 4) of hub 230. As can be seen in FIGS. 10A and 10B, each of the outer and inner connectors 410, 412 define an arcuate shape in cross section with respect to a plane that is perpendicular to the central axis A.

As can be seen in FIG. 10A, the arcuate shape of outer connector 410 is defined by opposed, spaced apart, first and second ends 462, 464. As such, the outer connector 410 forms less than a full tubular member in cross section. In some embodiments, and as best viewed in FIG. 10A, the arcuate shape of outer connector 410 comprises a C-shape in cross section. In some embodiments, the C-shape is defined by opposed ends 462, 464 spaced around the surface 422 less than 180 degrees. In further embodiments, the C-shape may be defined by opposed ends 462, 464 spaced approximately 180 degrees around surface 422 while in still further embodiments, opposed ends 462, 464 are spaced greater than 180 degrees around the outer surface 422 of inner connector 412 (See FIGS. 9A, 9B).

Likewise, and as can be seen in FIG. 10B, the arcuate shape of inner connector 412 is defined by opposed, spaced apart, first and second ends 562, 564. As such, the inner connector 412 forms less than a full tubular member in cross section. In some embodiments, and as best viewed in FIG. 10B, the arcuate shape of inner connector 412 comprises a C-shape in cross section. In some embodiments, the C-shape is defined by opposed ends 562, 564 spaced around the surface 422 less than 180 degrees. In further embodiments, the C-shape may be defined by opposed ends 562, 564 spaced approximately 180 degrees around surface 422 while in still further embodiments, opposed ends 562, 564 are spaced greater than 180 degrees around the outer surface 231 of hub member 230 (FIG. 4).

Regardless, and as illustrated in FIGS. 10A and 10B, each of the outer connector 410 and inner connector 412, when viewed in cross section along an entirety of their respective lengths L2 and L3 (FIG. 5) and with respect to a plane that is perpendicular to the central axis A, define a maximum distance D2 and D3, respectively, from the central axis A that includes conductive material such that, for respective circles C2 and C3 having an origin at the central axis A and a circumference at the respective maximum distances D2, D3, there exists at least one sector S-2, S-3 of the respective circles C2, C3 free of conductive material. In the illustrative embodiment, the sector S-2 is bounded by arc S1-2 and radii S2-2 and S3-2. In a similar manner, the sector S-3 is bounded by arc S1-3 and radii S2-3 and S3-3.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A blade assembly extending from a proximal region to a distal region, comprising:
    an outer shaft assembly including an outer shaft defining a lumen extending along a central axis, an outer circumference, a proximal end and a distal end opposite the proximal end, wherein the distal end defines a cutting window in the outer shaft assembly and a first electrode surface;
    an inner shaft assembly rotatably disposed within the lumen of the outer shaft assembly about the central axis, the inner shaft assembly defining a distal portion, the distal portion further including a cutting tip;
    an electrode body extending along the outer circumference and electrically isolated from the outer shaft, the electrode body defining a U-shape in cross section with respect to a plane that is perpendicular to the central axis and a second electrode surface spaced apart from the first electrode surface;
    a hub rotatably supporting the outer shaft and the electrode body, wherein upon rotation of the hub about the central axis, the outer shaft and the electrode body rotate about the central axis;
    a rotary electrical connection assembly comprising an outer connector and an inner connector rotatably disposed within the outer connector, the inner connector electrically connected to the electrode body;
    an irrigation channel fluidly coupled with the hub and configured to deliver fluid from the proximal region to the distal region; and
    wherein each of the outer connector, the inner connector and the electrode body are formed of a conductive material and extend a respective length in a direction parallel to the central axis, and further wherein, when viewed in cross section along an entirety of the respective length and with respect to the plane that is perpendicular to the central axis, each define a maximum distance from the central axis that includes conductive material such that, for a circle having an origin at the central axis and a circumference at the maximum distance, there exists at least one sector of the circle free of conductive material.

2. The blade assembly of claim 1, wherein the electrode body includes an inner surface facing the outer shaft and an outer surface opposite the inner surface and wherein the blade assembly further includes an insulating body covering the outer surface of the electrode body and the outer circumference of the outer shaft.

3. The blade assembly of claim 2, wherein the insulating body is heat shrink tubing.

4. The blade assembly of claim 1, further comprising wherein the irrigation channel is positioned between the outer circumference of the outer shaft and the electrode body.

5. The blade assembly of claim 4, wherein the electrode body further defines a distal cup fluidly coupled with the irrigation channel, the distal cup directing fluid from the irrigation channel between the first electrode surface and the second electrode surface.

6. The blade assembly of claim 1, wherein the electrode body terminates at a position with respect to the hub that is closer to the distal end than the proximal end.

7. The blade assembly of claim 1, wherein the U-shape defines opposed ends spaced apart around the outer circumference approximately 180 degrees.

8. The blade assembly of claim 1, wherein the U-shape defines opposed ends spaced apart around the outer circumference less than 180 degrees.

9. The blade assembly of claim 1, wherein the U-shape defines opposed ends spaced apart around the outer circumference greater than 180 degrees.

10. The blade assembly of claim 1, further comprising an insulating coating positioned between the outer circumference of the outer shaft and the electrode body.

11. The blade assembly of claim 1, wherein the electrode body extends around the outer shaft to cover a distal-most tip of the outer shaft.

12. The blade assembly of claim 1, wherein the irrigation channel is defined by tubing positioned between the outer shaft and the electrode body, a wall of the tubing separating the irrigation channel from the outer circumference of the outer shaft and an inner surface of the electrode body.

13. The blade assembly of claim 12, wherein the tubing terminates at an outlet end located between the outer shaft and the electrode body, and further wherein the irrigation channel is open to a space between the outer shaft and the electrode body at the outlet end.

14. The blade assembly of claim 1, wherein the inner connector defines an incomplete circle in a plane perpendicular to the central axis along an entirety of the length of the inner connector in the direction parallel to the central axis.

15. The blade assembly of claim 1, wherein the inner connector defines a C-shape in a plane perpendicular to the central axis along an entirety of the length of the inner connector in the direction parallel to the central axis.

* * * * *